United States Patent [19]
Prahl et al.

[11] Patent Number: 6,014,204
[45] Date of Patent: Jan. 11, 2000

[54] MULTIPLE DIAMETER FIBER OPTIC DEVICE AND PROCESS OF USING THE SAME

[75] Inventors: Scott Alan Prahl; Steven Louis Jacques, both of Portland, Oreg.

[73] Assignee: Providence Health System, Portland, Oreg.

[21] Appl. No.: 09/012,884

[22] Filed: Jan. 23, 1998

[51] Int. Cl.[7] .......................... G01N 21/49; G01N 21/64
[52] U.S. Cl. .................... 356/73; 356/446; 600/310; 600/317; 600/342
[58] Field of Search .................. 356/73, 432–435, 356/338–343, 445, 446; 385/12, 115, 116, 117; 600/310, 316, 317, 318, 319, 320, 321, 323, 324, 325, 326, 327, 328, 329, 337, 342

[56] References Cited

U.S. PATENT DOCUMENTS

| | | |
|---|---|---|
| 5,229,841 | 7/1993 | Taranowski et al. . |
| 5,483,347 | 1/1996 | Hollmann . |
| 5,485,536 | 1/1996 | Islam . |
| 5,492,118 | 2/1996 | Gratton et al. . |
| 5,522,868 | 6/1996 | Buckley et al. . |
| 5,555,885 | 9/1996 | Chance . |
| 5,561,290 | 10/1996 | Strobel et al. . |
| 5,572,320 | 11/1996 | Reinties et al. . |
| 5,640,240 | 6/1997 | Butler et al. . |
| 5,880,826 | 3/1999 | Jung et al. .................. 356/73 |

*Primary Examiner*—F. L. Evans
*Attorney, Agent, or Firm*—Ingrid McTaggart

[57] ABSTRACT

A multiple diameter fiber optic device comprises one or more optical fibers that are used to irradiate light onto a tissue and to detect light back-scattered by the tissue wherein each fiber is used for both irradiation and detection. In the case of multiple fibers, the fibers typically are bundled together at the probe end of the bundle. The diameters and/or numerical apertures of the one or more fibers are selected to provide different sampling volumes within the tissue. More specifically, the diameter and/or numerical apertures of the one or more fibers are chosen to emphasize differences in light penetration into the tissue such that the diameter and/or numerical aperture of each fiber is related to the scattering and absorption path lengths in the tissue.

30 Claims, 4 Drawing Sheets

MULTIPLE DIAMETER FIBER OPTIC DEVICE AND PROCESS OF USING THE SAME

TECHNICAL FIELD

The present invention relates to a multiple diameter fiber optic device for analyzing a material, and more particularly, to a multiple diameter fiber optic device for measuring the absorption and reduced scattering properties of a material by detecting light through multiple effective diameters of one or more optical fibers. The effective diameter of the device may comprise the diameter, the numerical aperture, and/or the index of refraction of the optical fiber.

BACKGROUND OF THE INVENTION

The determination of optical properties of tissues is important in many fields of medicine. Spectroscopy of tissue provides information about the absorption and scattering properties of the tissue. Such information is useful for specifying dosimetry in a laser protocol and characterization of the tissue for diagnosis. A clinical device to determine the optical properties of the tissue requires a probe that allows simple, accurate and reproducible measurements. A measurement device may comprise a topical probe for taking measurements of the skin or oral cavities, an endoscopic or a laparoscopic device for taking measurements of the gastrointestinal tract, or an interstitial needle catheter for minimally invasive interstitial measurements of the liver and brain.

Two tissues with different scattering properties and identical absorbing properties will re-emit a different number of incident photons. Consequently, to make accurate in vivo measurements of the concentration of an optically absorbing pigment, e.g., hemoglobin, it is necessary to determine both the absorption and the scattering properties. A variety of such measurements have been described.

In one example, a source fiber irradiates a sample while a detection fiber at a distance from the source fiber receives the back-scattered radiation from the sample. Multiple measurements of the back-scattered light as a function of the distance of the detection fiber from the source fiber are used to calculate the absorption and scattering properties of the sample. The distance between the two fibers typically is approximately 5–10 millimeters (mm), and may be on the order of several centimeters (cm). This application requires multiple measurements with movement of the detection fiber between each measurement.

Another application uses a single fiber for illumination and detection. This allows only a single measurement to be made and, consequently, one cannot discriminate the scattering and absorption properties but only one lumped combination of both.

Yet another application involves taking multiple measurements using the time-dependence of light that is re-emitted by the sample. This method requires high speed light detectors and complicated equipment.

Still another application uses measurements of light modulated at multiple frequencies to determine the absorption and scattering coefficients of a sample. This application requires two light sources or manipulation of the light source between measurements.

SUMMARY OF THE INVENTION

Accordingly, an object of the present invention is to provide a multiple diameter fiber optic device that is simple to operate.

Another object of the present invention is to provide a multiple diameter fiber optic device that is relatively inexpensive to manufacture.

Yet another object of the present invention is to provide a multiple diameter fiber optic device that is small in size.

Still another object of the present invention is to provide a multiple diameter fiber optic device that provides accurate and reproducible results.

Accordingly, the present invention provides a multiple diameter fiber optic device comprising one or more optical fibers that are used to irradiate tissue with light and to detect light back-scattered by the tissue wherein each fiber is used for both irradiation and detection. In the case of multiple fibers, the fibers typically are bundled together at the probe end of the bundle so as to provide a device having a compact size. The diameters and/or numerical apertures of the fibers are selected to provide different sampling volumes within the tissue. More specifically, the diameter and/or numerical apertures of the fibers are chosen to emphasize differences in light penetration into the tissue such that the diameter and/or numerical aperture of each fiber is related to the scattering and absorption path lengths in the tissue. In the case of a single fiber, the fiber is optically connected to an adjustable aperture wherein sequential measurements are taken through the single fiber with the adjustable aperture positioned at a unique diameter for each measurement.

In a preferred embodiment, the device comprises two fibers wherein each fiber has a unique diameter. In another embodiment, the device comprises two fibers wherein each fiber has a unique numerical aperture or a unique refractive index. In yet another embodiment, the device comprises a single fiber with an adjustable diameter. In still another embodiment, the device comprises a single fiber with an adjustable numerical aperture.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION

Figure 1:
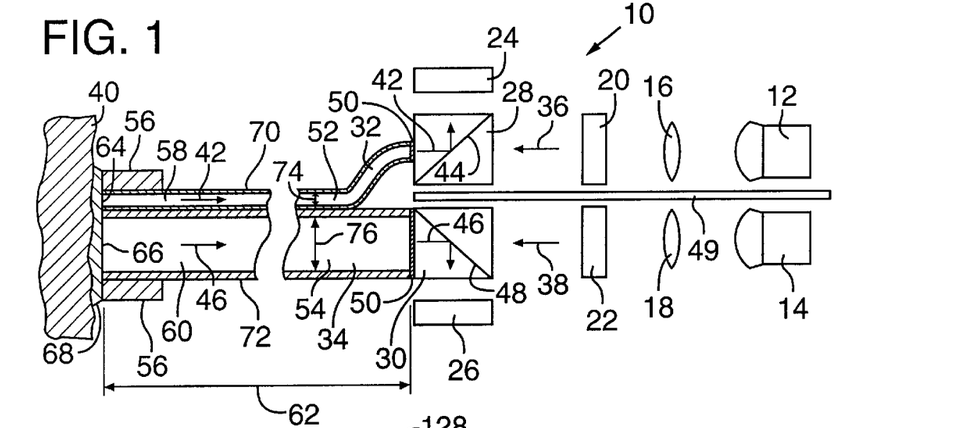
FIG. 1 is a partial cross sectional side view of the preferred embodiment of the multiple diameter fiber optic device of the present invention.

Referring to FIG. 1, which is a partial cross sectional side view of the preferred embodiment of the multiple diameter fiber optic device of the present invention, multiple diameter fiber optic device 10 comprises two light sources 12 and 14, two lens systems 16 and 18, two shutter systems 20 and 22, two detectors 24 and 26, two beam splitters 28 and 30, and two optical fibers 32 and 34, each of the fibers having a unique diameter. As will be understood by those skilled in the art, a single light source, lens system, and shutter system may be used to provide light sequentially to each of fibers 32 and 34.

Light sources 12 and 14 preferably each comprise a lamp that provides light beams 36 and 38 having a wavelength in the range of 200 to 11,000 nanometers (nm), and preferably in the range of 350 to 1,300 nm. Wavelengths below 200 nm are very strongly absorbed by proteins and the advantages of changes in the effective diameter are mitigated by the strong absorption. Wavelengths above 11,000 nm tend to be dominated by strong water absorption. In laboratory experiments, the light sources and the lens systems preferably provide a flat light profile to the fibers. In a manufacturing and mass production situation, the light sources and lens systems will preferably provide a Gaussian light profile to the fibers, due to the common use of Gaussian light profiles. In other embodiments, the light sources may comprise lasers, diodes, or other known light emitting devices, which may provide Gaussian or non-Gaussian light profiles.

Shutter systems 20 and 22 preferably comprise mechanical shutters that sequentially allow light from each of the sources to each of the corresponding optical fibers. In a preferred embodiment, shutter systems 20 and 22 comprise a single fan with multiple blades that rotates to sequentially illuminate the fibers. For example, as the fan rotates, an opening between blades (not shown) of the fan will permit source 12 to illuminate fiber 32 while one of the blades blocks the illumination of fiber 34. Upon further rotation of the fan, the opening will become aligned with fiber 34 while one of the blades blocks the illumination of fiber 32. The sequential illumination of each of fibers 32 and 34 is on the order of a fraction of a second so that multiple measurements can be taken through each individual fiber in a rapid time manner. In another embodiment, the shutter systems may comprise a diode timing mechanism, an optoacoustic shutter, an optoelectrical shutter or any other shutter as is known in the art. The shutter systems may be eliminated by turning light sources 12 and 14 on and off as needed.

Beam splitters 28 and 30 preferably comprise 2.5 centimeter (cm) square, non-polarizing dual prisms as known in the art. The prism must have a circumference that allows complete coverage of the optical fiber to which it is joined so as to receive all light re-emitted from the sample through each fiber. For example, beam splitter 28 permits light beam 36 to pass through the dual prisms, into fiber 32 and toward a tissue sample 40. Light 42 re-emitted from the tissue sample will be reflected by interface 44 of prism 28 and redirected toward detector 24. Similarly, beam splitter 30 permits light beam 38 to pass through the dual prisms, into fiber 34 and toward a tissue sample 40. Light 46 re-emitted from the tissue sample will be reflected by interface 48 of prism 30 and redirected toward detector 26. Detectors 24 and 26 preferably comprise spectrophotometers, but may also comprise photodiodes, photo multiplier tubes or any other known detection devices. An opaque blocking device 49 preferably extends between the light sources, lens systems, shutter systems and beam splitters so as to prevent the transmission of light there between.

In another embodiment, beam splitters 28 and 30 may each comprise a linear polarizer and a quarter-wave plate positioned at the tissue end of the fibers. Light will pass from the light sources through the linear polarizer and the quarter-wave plate to create circularly polarized light within the optical fibers. Specular reflection from the tissue sample will retain most of its polarization. The quarter-wave plate will rotate, therefore, the specularly reflected circular polarization to linear polarized light that is perpendicular to the linear polarizer. In this manner, the specular reflection from the tissue sample will be blocked from reaching the detectors. Accordingly, as will be more fully described below, light back-scattered from within the tissue will be detected by the light detectors.

Still referring to FIG. 1, fibers 32 and 34 are each coupled at their detector ends 52 and 54, respectively, to their respective beam splitter by an optical coupling device 50. As known in the art, any known optical coupling device, such as optical coupling epoxy or indexing matching fluid, may be used to minimize the detrimental effect of the transition of the light traveling between the beam splitters and the optical fibers. Fibers 32 and 34 preferably are held directly adjacent each other within a holder 56 at their probe ends 58 and 60, respectively. Due to the close proximity of the fibers, the fibers define essentially a point source of light on or in the tissue sample. The fibers typically each have a length 62 of approximately 2 meters (m). Any length of fiber maybe used, however, as is required in individual clinical situations so as to allow positioning of the holder on or into a tissue sample.

The flat ends 64 and 66 of the fibers preferably define a plane that is generally perpendicular to the length of the fibers. During topical use of the device, the flat ends of the fibers within holder 56 are placed on tissue sample 40 with an optical coupling solution 68 positioned there between. The optical coupling solution preferably comprises glycerin, but may also comprise water or oil. The optical coupling solution tends to eliminate air pockets between the optical device and the tissue sample so as to minimize the specular reflection detected by detectors 24 and 26 from the tissue sample. For purposes of this document, the term "tissue" includes all materials that one may wish to analyze to determine its absorption and reduced scattering characteristics. For example, the term tissue may include living materials, but may also include non-living materials such as emulsions.

In the preferred embodiment, fibers 32 and 34 comprise quartz fibers each having a flexible outer cladding 70 and 72, respectively. In other embodiments, the dual fiber bundle may comprise hollow core light guides, or any known optical transmitting device as is known in the art. The fibers preferably each have a unique diameter in the range of 1 to 2,000 micrometers ($\mu$m), and preferably in the range of 50 to 1000 $\mu$m. The different diameter of each fiber defines, therefore, a different effective diameter for each fiber. For example, in the preferred embodiment, fiber 32 has a core diameter 74 of approximately 200 $\mu$m and fiber 34 has a core diameter 76 of approximately 600 $\mu$m. The diameter of each of the fibers is comparable to the scattering and/or absorption path lengths in the tissue sample, as will be discussed below.

To calibrate device 10, a front surface mirror (not shown) is placed adjacent to flat end 64 of fiber 32 which is illuminated by light source 12. The light reflected (Vmirror) by the front surface mirror back into the fiber is collected by light detector 24. A second calibration point is achieved by placing a completely absorbing surface (not shown) adjacent the flat end 64 of fiber 32 which is illuminated by light source 12. The light reflected (Vblack) by the completely absorbing surface back into the fiber is collected by light detector 24. Once these calibration points have been determined, the flat end of fiber 32 is placed adjacent a tissue sample, the fiber is illuminated and the light back-scattered (Vscatter) by the tissue back into fiber 32 is collected by detector 24. The measurement and the two calibration points are sent to a computer (not shown) for analysis. The measurement and the two calibration points are used to convert the signal from the detector to a fraction (Rfiber1) of light returned from tissue sample 40 through fiber 32 by use of the equation Rfiber1=(Vscatter−Vblack)/((Vmirror−Vblack). This same technique is used to determine the fraction (Rfiber2) of light returned from tissue sample 40 through fiber 34. By use of these two measured fractions of light returned from the tissue sample, which may also be thought of as collection efficiencies (collected light/delivered light), two unknowns can be determined, namely the absorption and reduced scattering coefficients of the tissue sample. Use of more than two fibers in the fiber bundle, wherein at least two of the fibers have a unique diameter, will lead to more than two measurements to determine the two unknowns thereby providing for redundancy in the technique. Such redundancy increases the accuracy of the measurements and makes for a more robust device. Determination of the absorption and reduced scattering coefficients of the tissue sample allows one to determine the exact nature of the sample, for example, a determination of whether the tissue is abnormal or healthy. More specifically, the device may be used in a clinical setting to measure port wine stains before and after treatment, or changes in the scattering properties of neoplastic tissues.

The device may also be used to determine fluorescence measurements to monitor photosensitizer levels during photodynamic therapy, and psoralen levels during psoriasis treatment. Fluorescence measurements are conducted by measuring light at the excitation wavelength using two or more effective diameters and also measuring the fluorescent light at one or more wavelengths. The data collected at the excitation wavelength is used to generate the optical properties and illuminated light field. By assuming that the scattering properties at the emission wavelength are equal to the scattering properties at the excitation wavelength, or by use of a known function relating the scattering properties at the emission wavelength to the scattering properties at the excitation wavelength, the two measurements at the emission wavelength may be used to calculate the fluorescence efficiency and the absorption properties at the emission wavelength. The measurements at the emission and the excitation wavelengths may be taken sequentially or simultaneously, depending on the detector used. In one embodiment, the detector may comprise a spectrograph.

Figure 2:
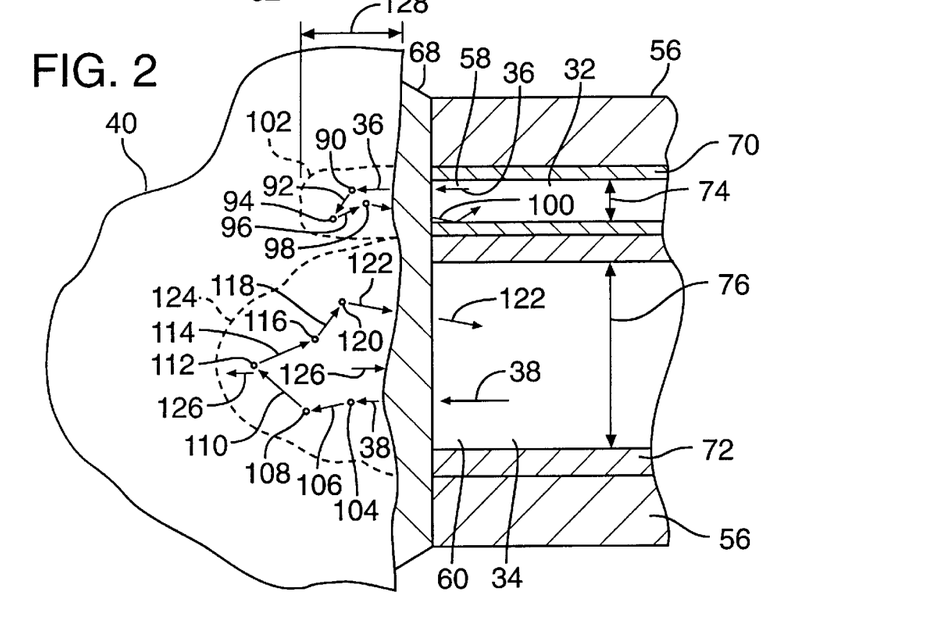
FIG. 2 is a detailed view of the interface of the fiber optic device of FIG. 1 with a tissue sample.

Referring to FIG. 2, which is a detailed view of the interface of the fiber optic device of FIG. 1 with a tissue sample, the scattering path of the light within the tissue sample will be described. Light 36 is emitted by source 12 and travels through fiber 32 to tissue sample 40. The light may strike a scattering site 90 and be scattered as light 92. Light 92 may strike a scattering site 94 and be scattered as light 96. Light 96 may strike a scattering site 98 and be scattered as light 100. Light 100 is within the diameter of fiber 32 and therefore is re-emitted into fiber 32 and detected by detector 24. The scattering sites may comprise particles such as cells or other tissue substructure but more probably comprise a fluctuation in the refractive index of the tissue sample. The path of light re-emitted by fiber 32 generally defines a volume 102 within tissue sample 40. As will be understood by those skilled in the art, changes in the direction of light due to refraction at an interface of two materials are known to occur but are not shown in the figures for ease of illustration.

Light 38 is emitted by source 14 and travels through fiber 34 to tissue sample 40. The light may strike a scattering site 104 and be scattered as light 106. Light 106 may strike a scattering site 108 and be scattered as light 110. Light 110 may strike a scattering site 112 and be scattered as light 114. Light 114 may strike a scattering site 116 and be scattered as light 118. Light 118 may strike a scattering site 120 and be scattered as light 122. Light 122 is within the diameter of fiber 34 and therefore is re-emitted into fiber 34 and detected by detector 26. The path of light re-emitted by fiber 34 generally defines a volume 124 within tissue sample 40.

Light scattering volumes 102 and 124 are each related to the diameter of their corresponding optical fiber because photons of light tend to spread throughout the volume of tissue adjacent to the surface area of the fiber as defined by the fiber's diameter. Accordingly, volume 124 is larger in diameter than is volume 102 because diameter 76 of fiber 34 is larger than diameter 74 of fiber 32. In addition, volume 124 is larger along its depth 126 than a depth 128 of volume 102 because photons of light collected by larger diameter fibers tend to travel deeper into the tissue sample than do photons collected by smaller diameter fibers. In other words, the collection efficiencies of the two fibers are different since light spreads differently under each fiber in the tissue and the different size fibers each collect different fractions of the total amount of reflected light. More specifically, the fraction of light re-emitted into a fiber increases as the size of the fiber is increased. Accordingly, by use of a multiple diameter fiber bundle reflectometry probe, multiple light collection efficiencies can be determined within a small tissue surface area without moving the fiber bundle over the tissue sample between each of the multiple measurements. Moreover, by use of more than two fibers in the probe bundle, more than two measurements can be made without moving the probe, thereby providing for an accurate and robust measurement device. The simplest device will comprise, of course, two fibers of unique diameters to determine the two unknowns, i.e., the absorption and the reduced scattering coefficients.

Figure 3:
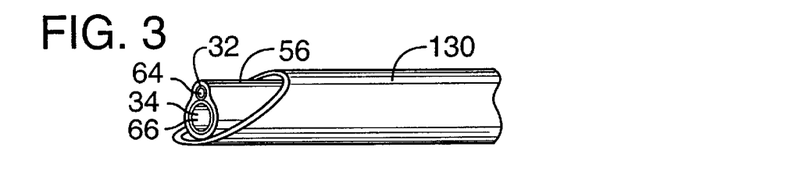
FIG. 3 is a perspective view of the preferred embodiment of the multiple diameter fiber optic device positioned within a needle.

Referring to FIG. 3, which is a perspective view of the preferred embodiment of the multiple diameter fiber optic device positioned within a needle, fibers 32 and 34 are shown positioned within a needle 130. Needle 130 may be used to insert the probe end of the fibers deep into a tissue sample so as to position the flat ends 64 and 66 of the fibers adjacent tissue to be measured. For example, needle 130 may be used to take interstitial measurements of the optical properties of liver or brain tissue. In another embodiment, the fibers may be positioned within a catheter to take endoscopic or laparoscopic measurements of the optical properties of gastrointestinal tract tissue.

Figure 4:
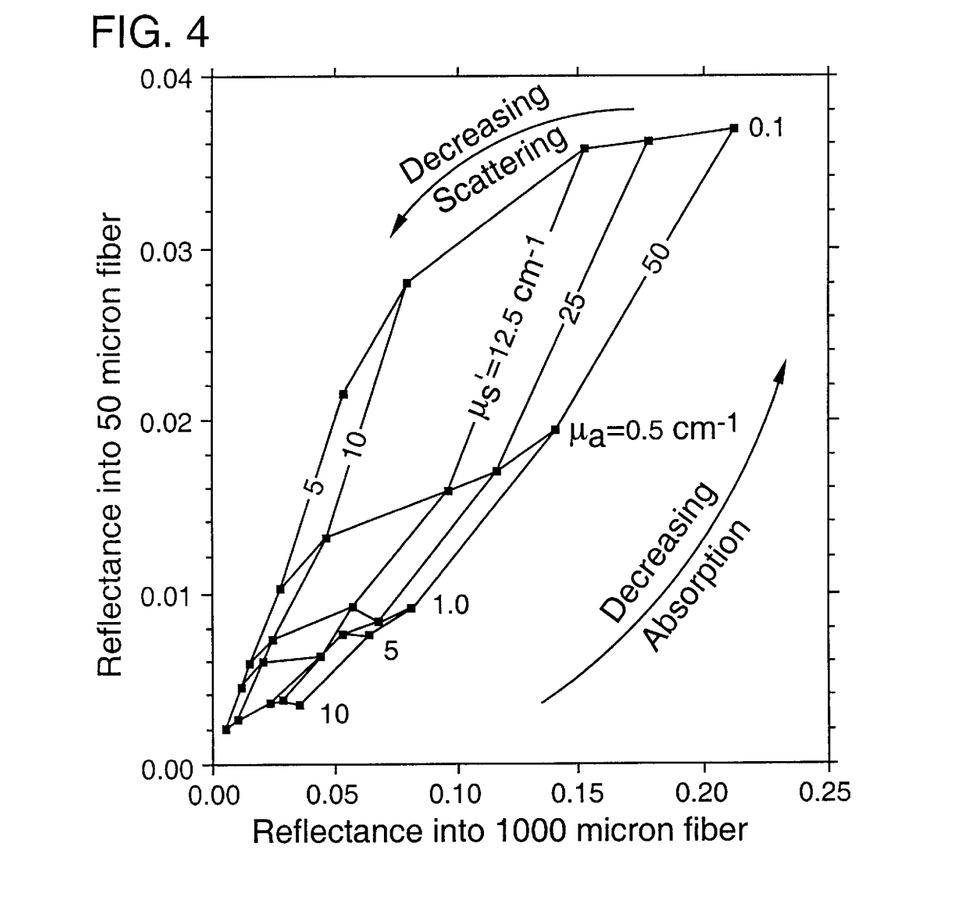
FIG. 4 is a calibration grid created for use with the multiple diameter fiber optic device.

Referring to FIG. 4, which is a calibration grid created for use with the multiple diameter fiber optic device, creation of the grid will be described. Simulations of light were emitted through and then re-emitted back into a 50 μm diameter fiber and a 1000 μm diameter fiber. The reflectance of each of the fibers was determined as the ratio of the light collected by the fiber to the light delivered through the fiber. The glitches in the grid are the result of using only 20,000 photons in a Monte Carlo simulation. For reasons of simplicity, the scattering in the sample material was assumed to be isotropic. Use of the grid allows one to determine the absorption and scattering coefficients of a tissue sample by measuring the reflectance from the tissue sample through two different fiber optic effective diameters. A typical tissue sample would yield visible and near infrared measurements in the central region of FIG. 4.

Figure 5:
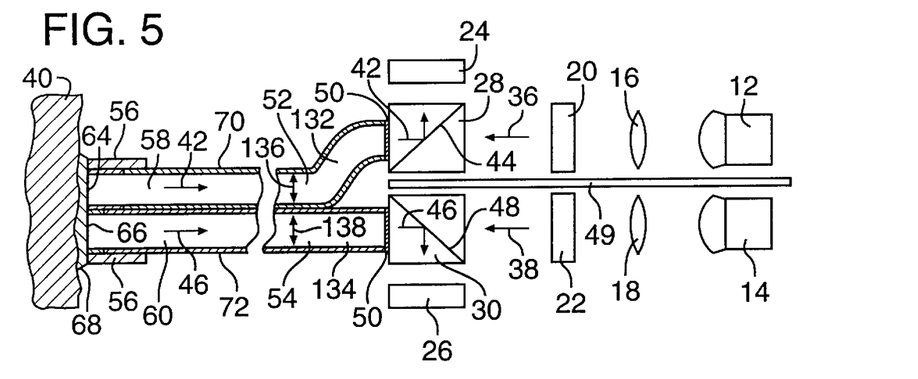
FIG. 5 is a partial cross sectional side view of a second embodiment of the multiple diameter fiber optic device of the present invention.

Referring to FIG. 5, which is a partial cross sectional side view of a second embodiment of the multiple diameter fiber optic device of the present invention, fiber 132 extends from beam splitter 28 and fiber 134 extends from beam splitter 30. In this embodiment, fiber 132 has a diameter 136 and fiber 134 has a diameter 138, wherein diameters 136 and 138 are both approximately 300 μm. Of course, other diameters may be utilized, as discussed above.

Figure 6:
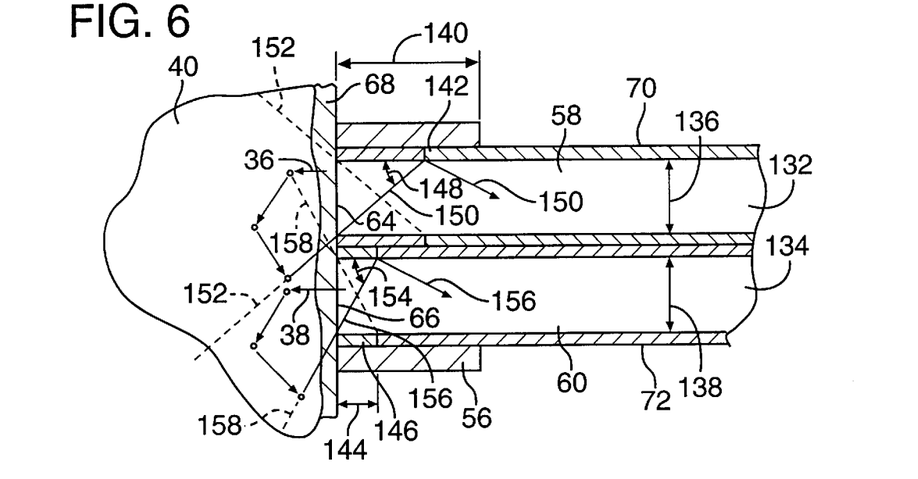
FIG. 6 is a detailed view of the interface of the fiber optic device of FIG. 5 with a tissue sample.

Referring to FIG. 6, which is a detailed view of the interface of the fiber optic device of FIG. 5 with a tissue sample, cladding 70 of fiber 132 is cut away along a length 140 of probe end 58. A second type of cladding 142 is positioned along length 140 of fiber 132 from flat end 64 of the fiber. Similarly, cladding 72 of fiber 134 is cut away along a length 144 of probe end 60. A second type of cladding 146 is positioned along length 144 of fiber 134 from flat end 66 of the fiber. In this embodiment, claddings 70 and 72 preferably are manufactured of the same material, claddings 142 and 146 preferably are manufactured of the same material, and claddings 70 and 72 are different from that of claddings 142 and 146. Those skilled in the art will understand that each of the claddings has a different refractive index from the refractive index of the core material of the optical fibers. In a variation of this embodiment, the refractive index of each of the fiber cores may be different. For example, one fiber core may be comprised of quartz while the other fiber core may be comprised of plastic. In another variation of this embodiment, the refractive index of the cladding of one fiber may be different from the refractive index of the corresponding cladding of another fiber. The different refractive index of the claddings or of the fiber cores defines, therefore, a different effective diameter for each optical fiber.

Claddings 142 and 146 preferably are both comprised of black absorbent material, such as paint, so that light contacting claddings 142 and 146 will not be re-emitted, respectively, through fibers 132 and 134 to detectors 24 and 26. Accordingly, fiber 132 defines an angle 148 that is the largest angle through which light 150 may be transmitted by fiber 132 to detector 24. Angle 148 in turn defines numerical aperture 152, also called the cone size, of fiber 132. Similarly, fiber 134 defines an angle 154 that is the largest angle through which light 156 may be transmitted by fiber 134 to detector 26. Angle 154 in turn defines numerical aperture 158, also called the cone size, of fiber 134. Because the fibers have the same diameters, and because length 140 is longer than length 146, angle 148 is smaller than angle 154, and numerical aperture 152 is smaller than numerical aperture 158.

Numerical apertures 152 and 158 are related to the amount of light re-emitted, respectively, into fibers 132 and 134. The different numerical aperture of each fiber, therefore, defines a different effective diameter for each fiber. Accordingly, as light of the same wavelength is sequentially transmitted along fibers 132 and 134, as discussed above with respect to the preferred embodiment, a single measurement can be taken through each of the two fibers with their unique effective diameters so as determine the two unknowns, i.e., the absorption and reduced scattering coefficients of the tissue sample. A variation of this embodiment may comprise claddings 142 and 146 manufactured of the same length, and the diameters of the fibers being of a different size, so as measure the two unknowns. Yet another variation of this embodiment may comprise claddings 142 and 146 each manufactured of a unique, non-absorbant material and extending along the entire length of each respective fiber, wherein the fibers may have similar diameters, so as to measure the two unknowns. In yet another variation, more than two fibers may be used so as to provide a redundant and robust measurement device. In still another embodiment, one of lengths 140 or 144 may be zero such that only one of the fibers has a second type of cladding, such as absorbent paint, at its probe end.

Figure 7:
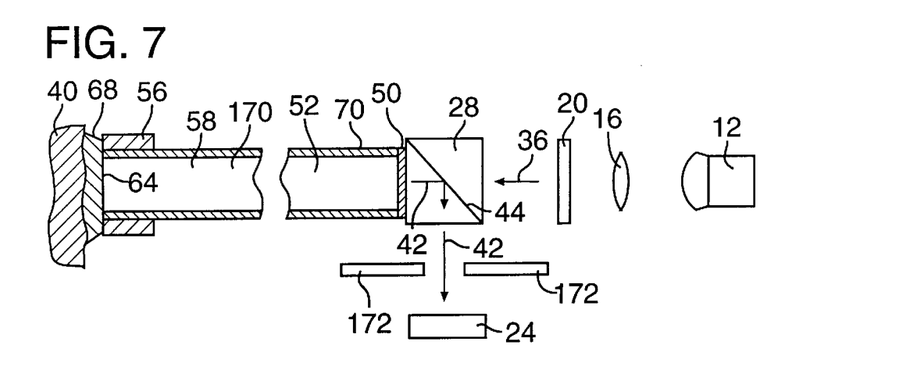
FIG. 7 is a partial cross sectional side view of a third embodiment of the multiple diameter fiber optic device of the present invention.

Referring to FIG. 7, which is a partial cross sectional side view of a third embodiment of the multiple diameter fiber optic device of the present invention, the device comprises a single optical fiber 170 and an adjustable aperture 172 positioned between beam-splitter 28 and detector 24. Adjustable aperture 172 preferably comprises a mechanically actuated adjustable iris, but may also comprise any device that provides an adjustable diameter aperture.

Figure 8:
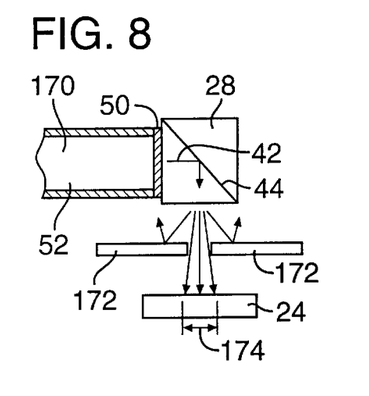
FIG. 8 is detailed view of the adjustable aperture of the device of FIG. 7 in a first position.

Referring to FIG. 8, which is detailed view of the adjustable aperture of the device of FIG. 7 in a first position, during a first measurement of light re-emitted through fiber 170 to detector 24, adjustable aperture 172 is in a first position and defines an aperture having a diameter 174. Diameter 174 defines a first numerical aperture, or cone size, of fiber 170.

Figure 9:
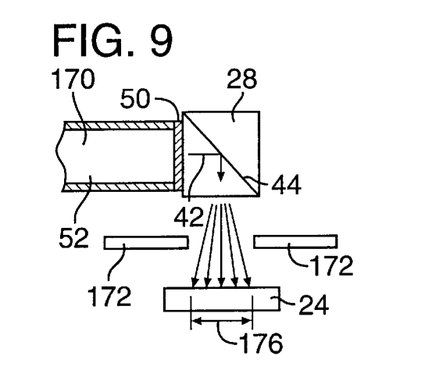
FIG. 9 is detailed view of the adjustable aperture of the device of FIG. 7 in a second position.

Referring to FIG. 9, which is detailed view of the adjustable aperture of the device of FIG. 7 in a second position, during a second measurement of light re-emitted through fiber 170 to detector 24, adjustable aperture 172 is in a second position and defines an aperture having a diameter 176. Diameter 176 defines a second numerical aperture, or cone size, of fiber 170. Accordingly, sequentially emitting light of the same wavelength through fiber 170, with adjustment of adjustable aperture 172 between the two measurements, allows for the determination of the two unknowns, i.e., the absorption and the reduced scattering coefficients of the tissue sample. In this embodiment, the angular information of light 142 traveling through the fiber during each measurement must be preserved. In other words, there must be no mode mixing of the light, such as a change in angle of the light, as it travels through fiber 170 for each measurement at detector 24. Such a change in angle may affect the light detected at detector 24 thereby providing an inaccurate reading.

Figure 10:
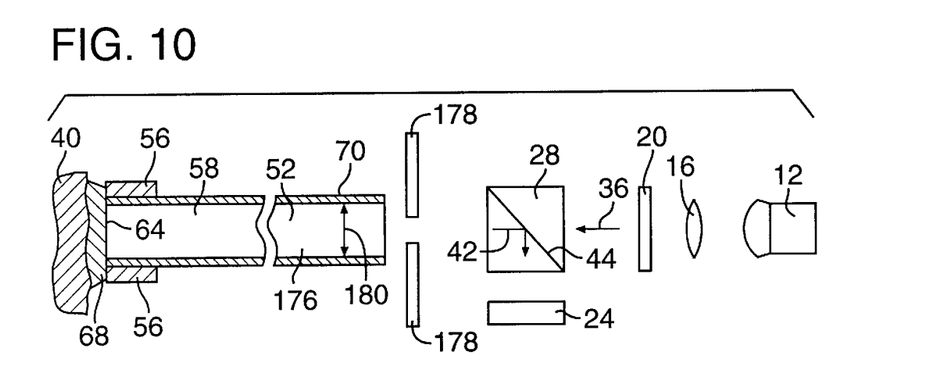
FIG. 10 is a partial cross sectional side view of a fourth embodiment of the multiple diameter fiber optic device of the present invention.

Referring to FIG. 10, which is a partial cross sectional side view of a fourth embodiment of the multiple diameter fiber optic device of the present invention, the device comprises a single optical fiber bundle 176 and an adjustable diaphragm 178 positioned between the beam splitter and the fiber bundle. Accordingly, the adjustable diaphragm is positioned such that light emitted from source 12 and re-emitted to detector 24 passes through the adjustable diaphragm. Fiber bundle 176 preferably comprises multiple fibers having a bundle diameter 180 of approximately 3 to 5 mm wherein each individual fiber typically has a diameter of approximately 1–10 μm. The multiple fiber bundle is coherent such that illumination of only the central fibers at detector end 52 will result in illumination at probe end 58 of the same central fibers of the bundle. Adjustable diaphragm 178 preferably comprises a mechanically actuated adjustable iris, but may also comprise any device that allows illumination and detection of a fixed fraction of fibers in the bundle at any given time.

Figure 11:
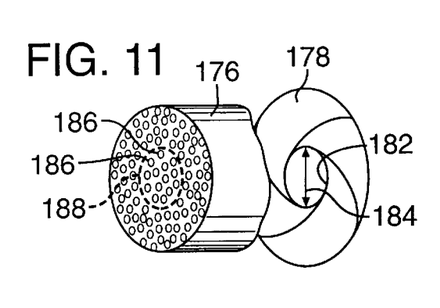
FIG. 11 is a detailed view of the adjustable diaphragm of the device of FIG. 10 in a first position.

Referring to FIG. 11, which is a detailed view of the adjustable diaphragm of the device of FIG. 10 in a first position, adjustable diaphragm 178 is in a first position and defines an aperture 182 having a diameter 184. Diameter 184 permits light source 12 to transmit light to individual optical fibers 186 within a first central region 188 of the optical fiber bundle. Diameter 184 also permits detector 24 to detect light from individual optical fibers 186 within first central region 188 of the optical fiber bundle. Accordingly, due to the coherent properties of the optical fiber bundle, the tissue sample is illuminated by fibers 186 that define the first effective diameter 188 of the bundle when the adjustable diaphragm is in the first position. For ease of illustration, several fibers 186 are shown as comprising the fiber bundle. Bundle 176 may comprise, however, several thousand individual fibers 186.

Figure 12:
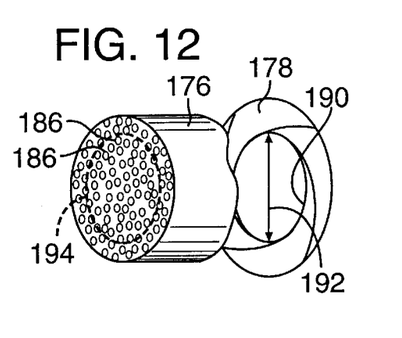
FIG. 12 is a detailed view of the adjustable diaphragm of the device of FIG. 10 in a second position.

Referring to FIG. 12, which is a detailed view of the adjustable diaphragm of the device of FIG. 10 in a second position, adjustable diaphragm 178 is in a second position and defines an aperture 190 having a diameter 192. Diameter 192 permits light source 12 to transmit light to individual optical fibers 186 within a second central region 194 of the optical fiber bundle. Diameter 192 also permits detector 24 to detect light from individual optical fibers 186 within second central region 194 of the optical fiber bundle. Accordingly, due to the coherent properties of the optical fiber bundle, the tissue sample is illuminated by fibers 186 that define the second effective diameter 194 of the bundle when the adjustable diaphragm is in the second position. Accordingly, sequentially emitting light of the same wavelength through fiber bundle 176, with adjustment of adjustable diaphragm 178 between the two measurements, allows for the determination of the two unknowns, i.e., the absorption and the reduced scattering coefficients of the tissue sample.

While preferred embodiments of the present invention have been shown and described, it will be apparent to those skilled in the art that many changes and modifications may be made without departing from the invention in its broader aspects. The appended claims are intended to cover, therefore, all such changes and modifications as fall within the true spirit and scope of the invention.

We claim:

1. A device for measuring the absorption and reduced scattering properties of a material, comprising:
   a light source capable of emitting light therefrom;
   a light detector capable of detecting light transmitted thereto; and
   a fiber optic array including a first optical fiber having a first effective diameter and a second optical fiber having a second effective diameter wherein said first effective diameter is different than said second effective diameter and wherein said first optical fiber transmits said light from said source to a material and thereafter transmits light re-emitted from said material to said detector through said first effective diameter and wherein said second optical fiber transmits said light from said source to the material and thereafter transmits light re-emitted from said material to said detector through said second effective diameter wherein the light transmitted by said first and second optical fibers from the material to the detector facilitates measurement of the absorption and reduced scattering properties of the material.

2. A device according to claim 1 wherein said first effective diameter is the diameter of the first optical fiber and wherein said second effective diameter is the diameter of the second optical fiber.

3. A device according to claim 1 wherein said first and second effective diameters are numerical apertures.

4. A device according to claim 1 wherein said fiber optic array is positioned within an endoscopic catheter.

5. A device according to claim 1 wherein said fiber optic array is positioned within a holder adapted for topical use.

6. A device according to claim 1 wherein said fiber optic array is positioned within a needle.

7. A device according to claim 1 wherein said light detector is capable of detecting fluorescence.

8. A device according to claim 1 wherein said detector measures the absorption and reduced scattering properties of the material based on light transmitted to the detector through said first and second effective diameters.

9. A process for analyzing a material, comprising:
   emitting light onto a material through an optical fiber having a first effective diameter;
   measuring the amount of light re-emitted from the material through the optical fiber having said first effective diameter;
   emitting light onto the material through an optical fiber having a second effective diameter; and
   measuring the amount of light re-emitted from the material through the optical fiber having said second effective diameter, wherein the second effective diameter is different from the first effective diameter.

10. A process according to claim 9 wherein the light is emitted from a single source.

11. A process according to claim 10 wherein the single source emits light at a single wavelength.

12. A process according to claim 11 wherein light is emitted onto the material through a single optical fiber that is operatively connected to an adjustable aperture that is adjustable between said first effective diameter and said second effective diameter, further comprising adjusting the adjustable aperture between each step of measuring light re-emitted from the material.

13. A process according to claim 12 wherein said adjustable aperture comprises a mechanically actuated adjustable iris positioned between said single optical fiber and a light detector.

14. A process according to claim 9 wherein light is emitted onto the material through a coherent bundle of multiple fibers that is operatively connected to an adjustable aperture that is positioned between a light source and said bundle of multiple fibers, further comprising adjusting the adjustable aperture between each step of measuring light re-emitted from the material.

15. A process according to claim 9 wherein the optical fiber including the first effective diameter is separate from the optical fiber including the second effective diameter.

16. A process according to claim 15 wherein said first effective diameter comprises a first numerical aperture and said second effective diameter comprises a second numerical aperture.

17. A process according to claim 12 wherein said adjustable aperture comprises a numerical aperture.

18. A process according to claim 9 further comprising using the measured amount of light re-emitted through the first effective diameter and the measured amount of light re-emitted through the second effective diameter to determine the absorption and scattering characteristics of the material.

19. A process according to claim 9 wherein said optical fiber having said first effective diameter and said optical fiber having said second effective diameter together comprise a fiber optic array, further comprising placing said fiber optic array in an endoscopic catheter prior to emitting light through the fiber optic array.

20. A process according to claim 9 wherein said optical fiber having said first effective diameter and said optical fiber having said second effective diameter together comprise a fiber optic array, further comprising placing the fiber optic array in a holder adapted for topical use prior to emitting light through the fiber optic array.

21. A process according to claim 9 wherein said optical fiber having said first effective diameter and said optical fiber having said second effective diameter together comprise a fiber optic array, further comprising placing the fiber optic array in a needle prior to emitting light through the fiber optic array.

22. A process according to claim 9 wherein the step of measuring the amount of light re-emitted from the material includes measuring fluorescence.

23. A device for measuring the absorption and reduced scattering properties of a material, comprising:
   a light source capable of emitting light therefrom;
   a light detector capable of detecting light transmitted thereto; and
   a fiber optic assembly that transmits light from said light source to a material through a first effective diameter and thereafter transmits light re-emitted from said material through said first effective diameter to said light detector, and transmits light from said light source to the material through a second effective diameter and thereafter transmits light re-emitted from said material through said second effective diameter to said light detector, wherein said first effective diameter is different than said second effective diameter, and wherein light transmitted through said first and second effective diameters facilitates measurement of the absorption and reduced scattering properties of the material.

24. A device according to claim 23 wherein said fiber optic assembly comprises first and second optical fibers, and wherein said first optical fiber includes said first effective diameter and said second optical fiber includes said second effective diameter.

25. A device according to claim 23 wherein said fiber optic assembly comprises a single optical fiber and an adjustable aperture that is adjustable between said first and second effective diameters.

26. A device according to claim 25 wherein said adjustable aperture comprises a mechanically actuated adjustable iris positioned between said optical fiber and said detector.

27. A device according to claim 23 wherein said fiber optic assembly comprises a coherent bundle of optical fibers and an adjustable aperture and wherein said adjustable aperture is positioned between said source and said bundle of optical fibers.

28. A device according to claim 24 wherein said first effective diameter is the diameter of the first optical fiber and wherein said second effective diameter is the diameter of the second optical fiber.

29. A device according to claim 23 wherein said detector measures the absorption and reduced scattering properties of the material based on light transmitted to the detector through said first and second effective diameters.

30. A device according to claim 23 wherein said light source comprises two lamps and wherein said detector comprises two detection devices.

* * * * *